US011612452B2

(12) United States Patent
Leclere et al.

(10) Patent No.: US 11,612,452 B2
(45) Date of Patent: Mar. 28, 2023

(54) SYSTEMS AND METHODS FOR PERISTALTIC ENDOSCOPE CLEANING

(71) Applicant: Stryker Corporation, Kalamazoo, MI (US)

(72) Inventors: Theodore Leclere, San Francisco, CA (US); Candice Pack, Campbell, CA (US)

(73) Assignee: Stryker Corporation, Kalamazoo, MI (US)

( * ) Notice: Subject to any disclaimer, the term of this patent is extended or adjusted under 35 U.S.C. 154(b) by 31 days.

(21) Appl. No.: 17/082,991

(22) Filed: Oct. 28, 2020

(65) Prior Publication Data

US 2021/0121266 A1    Apr. 29, 2021

Related U.S. Application Data

(60) Provisional application No. 62/926,823, filed on Oct. 28, 2019.

(51) Int. Cl.
*A61B 90/70* (2016.01)
*B08B 9/023* (2006.01)
*F04B 43/12* (2006.01)
*F04B 49/06* (2006.01)

(52) U.S. Cl.
CPC .............. *A61B 90/70* (2016.02); *B08B 9/023* (2013.01); *F04B 43/1253* (2013.01); *F04B 49/06* (2013.01); *A61B 2090/701* (2016.02)

(58) Field of Classification Search
CPC ..... A61B 1/126; A61B 1/015; A61B 1/00135; A61B 1/00142; A61B 90/70; A61B 2090/701; A61B 1/00–32; B08B 9/023; B08B 3/00–14; B08B 9/00–46; F04B 43/12–1292
See application file for complete search history.

(56) References Cited

U.S. PATENT DOCUMENTS 5,053,002 A * 10/1991 Barlow .............. A61B 1/00135
                                                    604/245
5,484,402 A *  1/1996 Saravia ................ A61M 1/7415
                                                    604/35

(Continued)

OTHER PUBLICATIONS

Richard Beverly, Pump Selection & Troubleshooting Field Guide, Ch. 5.2.2 Peristaltic Pumps (American Water Works Association 2009), available at https://app.knovel.com/hotlink/pdf/id:kt0087Y7S1/pump-selection-troubleshooting/peristaltic-pumps (Year: 2009).*

(Continued)

*Primary Examiner* — Mikhail Kornakov
*Assistant Examiner* — Richard Z. Zhang
(74) *Attorney, Agent, or Firm* — Morrison & Foerster LLP

(57) ABSTRACT

The present disclosure is directed to endoscope cleaning systems and methods. The endoscope cleaning system can include a pump housing that houses a peristaltic pump, an endoscope sheath fluidly connected to the pump housing, and a pump control communicatively coupled to the peristaltic pump. Upon activation of the pump control, the peristaltic pump can supply fluid to the endoscope sheath for cleaning an endoscope. Upon deactivation of the pump control, the peristaltic pump can remove residual fluid from the endoscope.

27 Claims, 10 Drawing Sheets

(56) References Cited

U.S. PATENT DOCUMENTS

| | | | |
|---|---|---|---|
| 6,106,494 A * | 8/2000 | Saravia | A61M 3/0258 |
| | | | 604/151 |
| 6,110,103 A | 8/2000 | Donofrio | |
| 6,126,592 A * | 10/2000 | Proch | A61B 1/127 |
| | | | 600/129 |
| 6,447,446 B1 * | 9/2002 | Smith | A61B 1/00142 |
| | | | 600/118 |
| 2008/0132763 A1 | 6/2008 | Isaacson | |
| 2011/0237880 A1 * | 9/2011 | Hamel | A61B 1/015 |
| | | | 600/104 |
| 2012/0035417 A1 | 2/2012 | Moellstam | |
| 2014/0261579 A1 | 9/2014 | Jenkins | |
| 2015/0005582 A1 * | 1/2015 | Poll | A61B 1/3132 |
| | | | 600/123 |
| 2015/0087909 A1 * | 3/2015 | Cheng | A61B 1/00142 |
| | | | 600/123 |
| 2016/0199565 A1 * | 7/2016 | Stubkjaer | A61M 1/0062 |
| | | | 604/28 |
| 2017/0296046 A1 | 10/2017 | King | |

OTHER PUBLICATIONS

International Search Report and Written Opinion dated Jan. 14, 2021, directed to International Application No. PCT/US2020/057730; 11 pages.

* cited by examiner

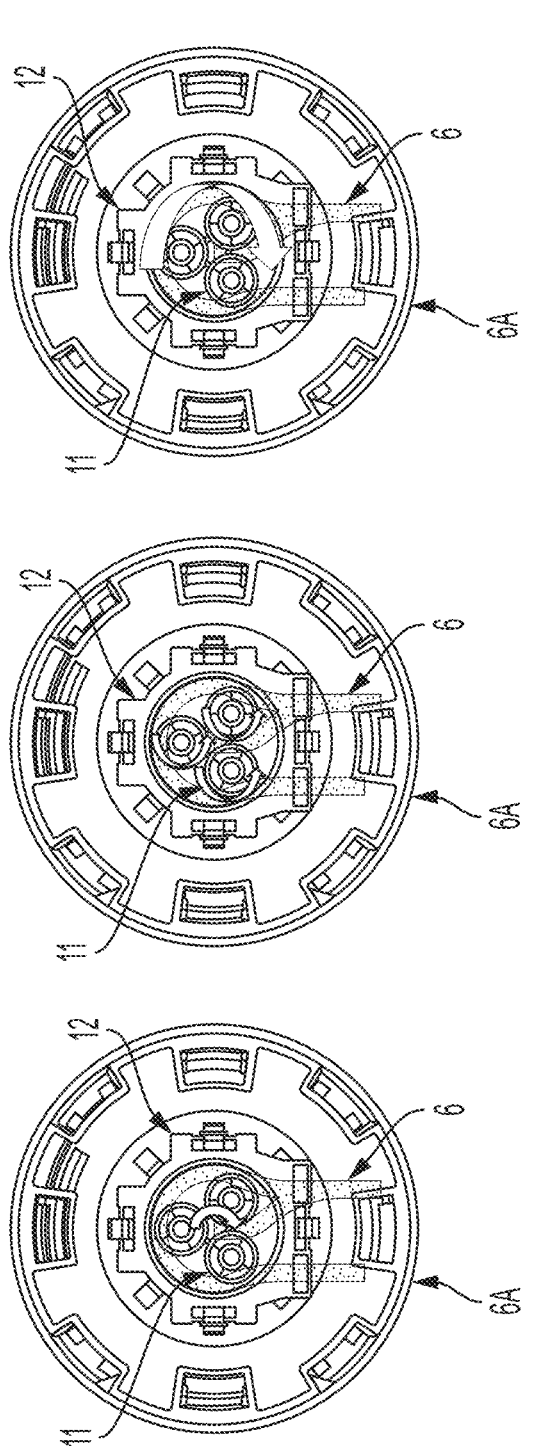

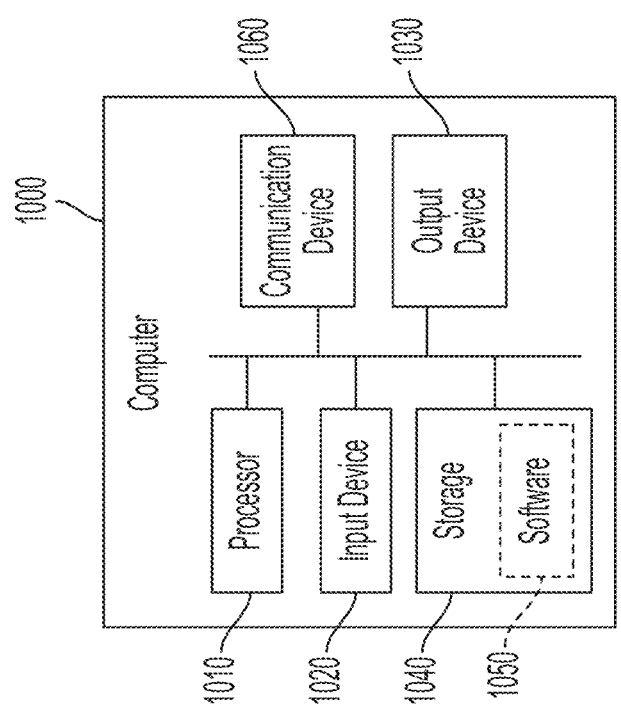

SYSTEMS AND METHODS FOR PERISTALTIC ENDOSCOPE CLEANING

CROSS-REFERENCE TO RELATED APPLICATIONS

This application claims the benefit of U.S. Provisional Application No. 62/926,823, filed Oct. 28, 2019, the entire contents of which are hereby incorporated by reference herein.

FIELD

This disclosure relates generally to an endoscope cleaning systems and methods, and more specifically, to self-contained endoscope cleaning systems and methods.

BACKGROUND

Typical endoscope cleaning systems for Ear, Nose, and Throat ("ENT") procedures have multiple components involving extensive set-up time to connect these multiple components to form the systems. In addition, these components are often expensive and require access to external power supplies in order for the system to function.

For example, a typical endoscope cleaning system can include one or two reusable, capital consoles that require external power for the pumping units. Tubing is also then separately connected to the pumping unit. Next, a disposable or reusable endoscope sheath can be connected to the tubing to complete the system. As such, only then can the pumping unit drive fluid to the endoscope cleaning sheath.

SUMMARY

According to an aspect, endoscope cleaning can be accomplished by an all-in-one pump, tubing, sheath, and pump control system, which may be optionally single-use. The endoscope cleaning system can simplify the set-up process for ENT operations as it is a self-powered (e.g., battery-powered), all-in-one pump, tubing, sheath, and pump control that can simply be connected to a fluid supply (e.g., a sterile irrigation bag) and can have an endoscope to be inserted into the sheath to be ready to use. Thus, besides coupled the fluid supply and the endoscope to the system, the endoscope cleaning system may not require any additional connections or external power supply for it to function.

According to an aspect, the endoscope cleaning system can include a self-contained pump housing, tubing, endoscope sheath, and activation solution for intraoperative cleaning of endoscopes during minimally invasive surgeries. The pump housing can include a hollow spike that can directly connect to a sterile fluid bag providing an inlet for the fluid as well as supporting the weight of the pump housing. The pump housing can include flexible tubing and peristaltic rollers to displace fluid, a motor to drive the rollers, and an electric battery assembly to drive the motor. In addition, the device can include a pump control to automatically regulate motor speed and direction. Tubing can extend from the pump housing towards an endoscope cleaning sheath. In addition, wiring can extend from the pump housing to the hand-controlled switch that can be connected to the endoscope cleaning sheath. Alternatively, wiring may be separate from the tubing and terminate with a foot-controlled switch rather than a hand-controlled switch. Upon activation of the switch, fluid can be supplied through the endoscope sheath to the distal end of the endoscope for the purpose of cleaning. When activation of the switch is released, the pump can withdraw fluid back towards the pump for a set period to remove fluid from the end of the endoscope.

According to an aspect, an endoscope cleaning system includes: a pump housing comprising a fluid inlet, a fluid outlet, and a peristaltic pump configured to displace fluid from the fluid inlet to the fluid outlet; an endoscope sheath fluidly connected to the fluid outlet of the pump housing, wherein the endoscope sheath is configured to receive an endoscope; and a pump control communicatively coupled to the peristaltic pump, wherein the pump control is configured to activate the peristaltic pump.

Optionally, the peristaltic pump in the pump housing comprises a plurality of peristaltic rollers, a motor to drive the rollers, and a power source to power the motor.

Optionally, the pump control is configured to regulate speed and direction of the motor.

Optionally, the power source is a battery assembly.

Optionally, the endoscope sheath and the fluid outlet of the pump housing are fluidly connected by tubing.

Optionally, the tubing is fluidly connected to a proximal end of the endoscope sheath.

Optionally, the pump control is attached to a distal end of the tubing.

Optionally, the pump control is attached to the tubing by the proximal end of the endoscope sheath.

Optionally, the endoscope sheath is configured to supply fluid to a distal end of an endoscope.

Optionally, the fluid inlet comprises a spike on a top surface of the pump housing.

Optionally, the spike is a hollow, tapered spike.

Optionally, the hollow, tapered spike is configured to be inserted into a fluid source.

Optionally, the fluid source is a sterile irrigation bag.

Optionally, the fluid outlet is perpendicular to the fluid inlet.

Optionally, the pump control is wirelessly communicatively coupled to the peristaltic pump.

Optionally, the pump control is a hand-controlled switch.

Optionally, the pump control is a foot-controlled switch.

Optionally, the peristaltic pump is configured to displace fluid from the fluid inlet to the fluid outlet upon activation of the pump control.

Optionally, the peristaltic pump is configured to displace fluid from the fluid outlet to the fluid inlet upon deactivation of the pump control.

According to an aspect, a method of cleaning an endoscope includes: activating a pump control; upon activation of the pump control, displacing, via a peristaltic pump, fluid from a fluid inlet to a fluid outlet of a pump housing, wherein an endoscope sheath configured to receive an endoscope is fluidly connected to the fluid outlet of the pump housing; deactivating a pump control; and upon deactivation of the pump control, displacing, via the peristaltic pump, fluid from the fluid outlet to the fluid inlet of the pump housing.

Optionally, upon activation of the pump control, the peristaltic pump displaces fluid from the fluid inlet to the fluid outlet at a first speed for a first period of time.

Optionally, while the pump control is activated and upon termination of the first period of time, the peristaltic pump displaces fluid from the fluid inlet to the fluid outlet at a second speed, wherein the second speed is less than the first speed.

Optionally, upon deactivation of the pump control, the peristaltic pump displaces fluid from the fluid outlet to the fluid inlet at a third speed for a second period of time.

Optionally, while the pump control is deactivated and upon termination of the second period of time, the peristaltic pump displaces fluid from the fluid outlet to the fluid inlet at a fourth speed, wherein the fourth speed is less than the third speed.

Optionally, the peristaltic pump displaces fluid from the fluid outlet to the fluid inlet at the fourth speed for a third period of time.

Optionally, upon termination of the third period of time, the peristaltic pump shuts off Optionally, the method includes inserting an endoscope into the endoscope sheath.

Optionally, the method includes inserting the fluid inlet of the pump housing into a fluid source.

Optionally, the fluid inlet is a hollow, tapered spike.

Optionally, the fluid source is a sterile irrigation bag.

Optionally, the pump control is communicatively coupled to the peristaltic pump.

Optionally, the pump control is wirelessly communicatively coupled to the peristaltic pump.

Optionally, while the pump control is activated, fluid is supplied from the endoscope sheath to a distal end of an endoscope.

Optionally, while the pump control is deactivated, fluid is removed from the distal end of the endoscope to the endoscope sheath.

It will be appreciated that any of the variations, aspects, features and options described in view of the systems apply equally to the methods and vice versa. It will also be clear that any one or more of the above variations, aspects, features and options can be combined.

Additional advantages will be readily apparent to those skilled in the art from the following detailed description. The aspects and descriptions herein are to be regarded as illustrative in nature and not restrictive.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

BRIEF DESCRIPTION OF THE FIGURES

Exemplary embodiments are described with reference to the accompanying figures, in which:

FIG. 7 illustrates a planetary motion diagram for the peristaltic pump used in the pump housing in accordance with some embodiments disclosed herein.

FIG. 10 depicts a computer, in accordance with some embodiments.

In the Figures, like reference numbers correspond to like components unless otherwise stated.

DETAILED DESCRIPTION

Figure 1:
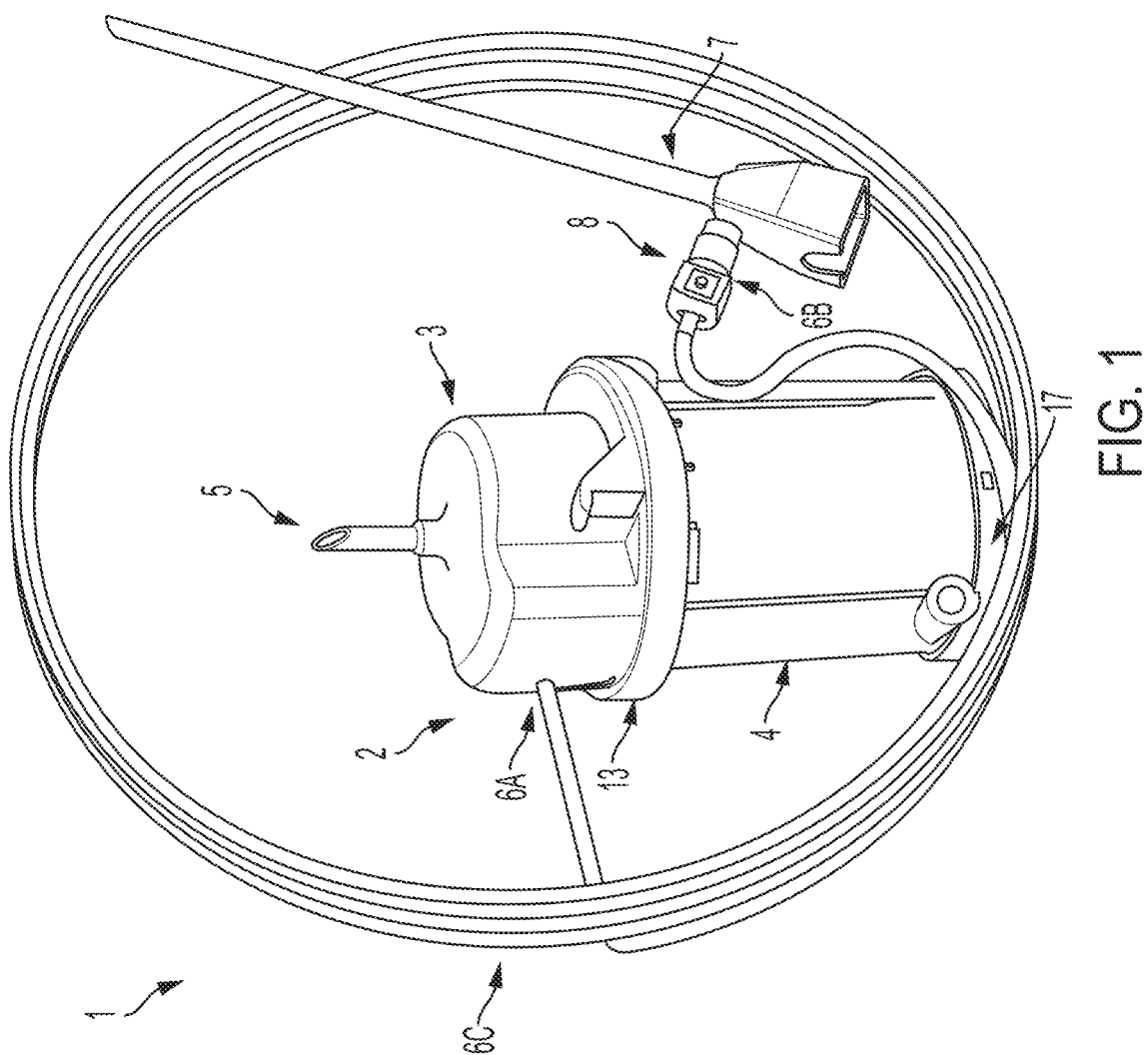
FIG. 1 illustrates an example of an all-in-one peristaltic endoscope cleaning system in accordance with some embodiments disclosed herein.

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Described herein are endoscopic cleaning systems and methods. According to some embodiments, the endoscopic cleaning system can include a self-contained pump housing, tubing, sheath, and pump control for intraoperative cleaning of endoscopes during endoscopic surgeries, which can be a single-use system. According to some embodiments, the system can be self-powered through a battery assembly and is ready-to-use (only requiring to be connected to a fluid supply (e.g., sterile irrigation bag)) to provide forward and reverse flow of fluid through an endoscope cleaning sheath. Tubing and wiring can extend from a pump housing, ending with a single use endoscope cleaning sheath and either a hand-controlled or foot-controlled switch. Upon activation of the switch, the pump can supply fluid through the endoscope cleaning sheath to the lens of an endoscope to clean off debris. When activation is released, the pump can automatically withdraw a small amount of fluid to remove any remaining fluid from the lens of the scope.

FIGS. 1-6 illustrate examples of various aspects of an all-in-one peristaltic endoscope cleaning system 1 in accordance with some embodiments disclosed herein. In some embodiments, the peristaltic system can be used for sinuscope cleaning for Ear, Nose, and Throat ("ENT") procedures to keep visualization through the sinuscope clear during procedures. Peristaltic system 1 can include pump housing 2. The pump housing can house the peristaltic pump that displaces fluid throughout the system.

The pump housing can be a single component or can be made up of multiple components. For example, the pump housing can include an upper housing member 3, a middle housing member 13, and a bottom housing member 4. The upper housing member can be coupled to the middle housing member and the middle housing member can be coupled to the bottom housing member. As such, these various housing members can be coupled or connected together to form the shell of the pump housing. In some embodiments, a portion of the upper housing member can overlap a portion of the middle housing member and/or a portion of the middle housing member can overlap a portion of the bottom housing member.

In some embodiments, the pump housing can include a bottom surface 17 that can be coupled to the bottom housing member. In some embodiments, the bottom housing member and the bottom surface are integral as a single component. The upper housing member can be the top most component of the pump housing. The upper housing member can include an inlet 5 on its upper most or top surface. The inlet can act as a fluid inlet into the pump housing. In some embodiments, the inlet can be fluidly connected to a fluid source. In some embodiments, the inlet is a spike. For example, the fluid source can be a sterile irrigation fluid bag and the pump housing's inlet can be directly spiked into the sterile irrigation fluid bag. The fluid source is not limited to an irrigation fluid bag, but can be a variety of fluid sources such as sterile saline solution bags or sterile water bags. In some embodiments, the inlet can be a hollow, tapered spike. The spike may not only provide a fluid inlet for the pump housing, but can also support the pump housing. For example, when the spike is inserted directly into a sterile irrigation fluid bag connector, the spike can support the pump housing which hangs beneath the bag due to the holding force from the spike within the connector. The connector typically can have an elastomer seal that the spike can pierce. Once pierced, the spike can be inserted further. In some embodiments, due to the external taper of the spike, the force required to insert the spike can be higher over the course of the insertion. Once inserted, the pump can be held in the connector due to friction force. With a tapered spike, the normal force can increase the further the spike is inserted due to the increasing external diameter which consequently increases the friction force. As long as the friction force is larger than the gravitational force on the pump, the pump can hang from the bag and not slip out. Alternatively, instead of inserting through an elastomer seal, the connector can also be a short flexible tube. The user can remove some sort of seal and then the inlet/spike can be inserted into the tubing end. The same concepts can apply to this type of connector as well.

Figure 2:
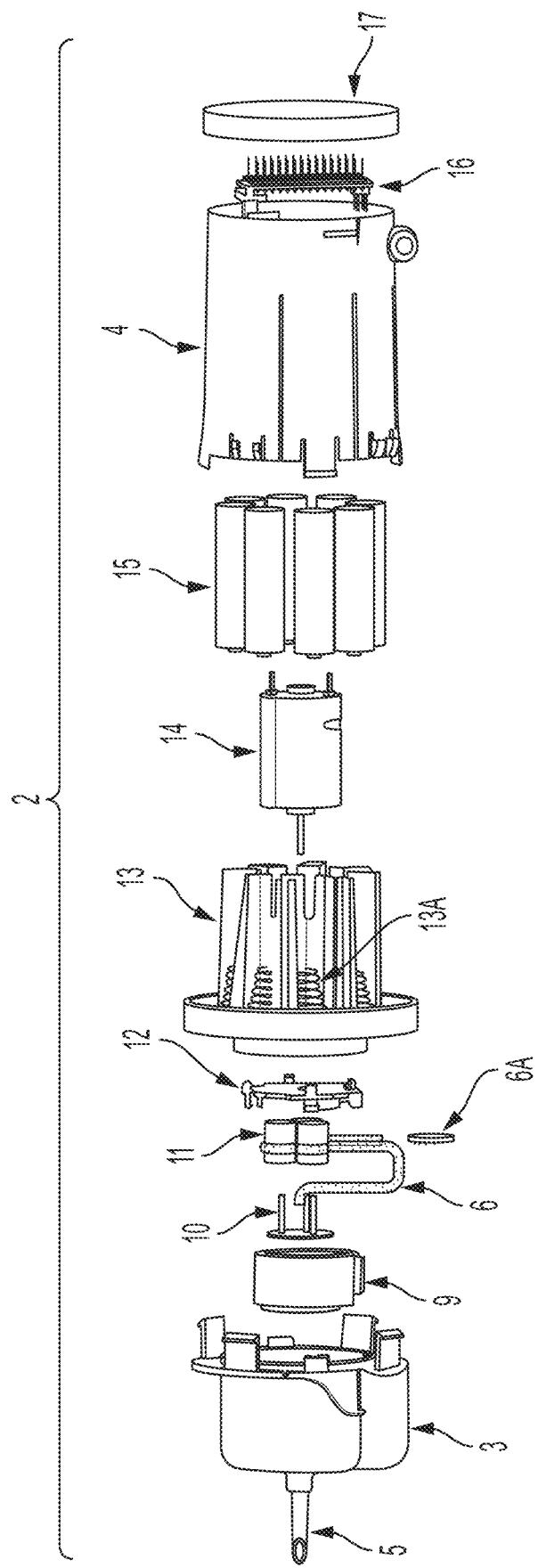
FIG. 2 illustrates an example of an exploded view of the pump housing in accordance with some embodiments disclosed herein.
Figure 3:
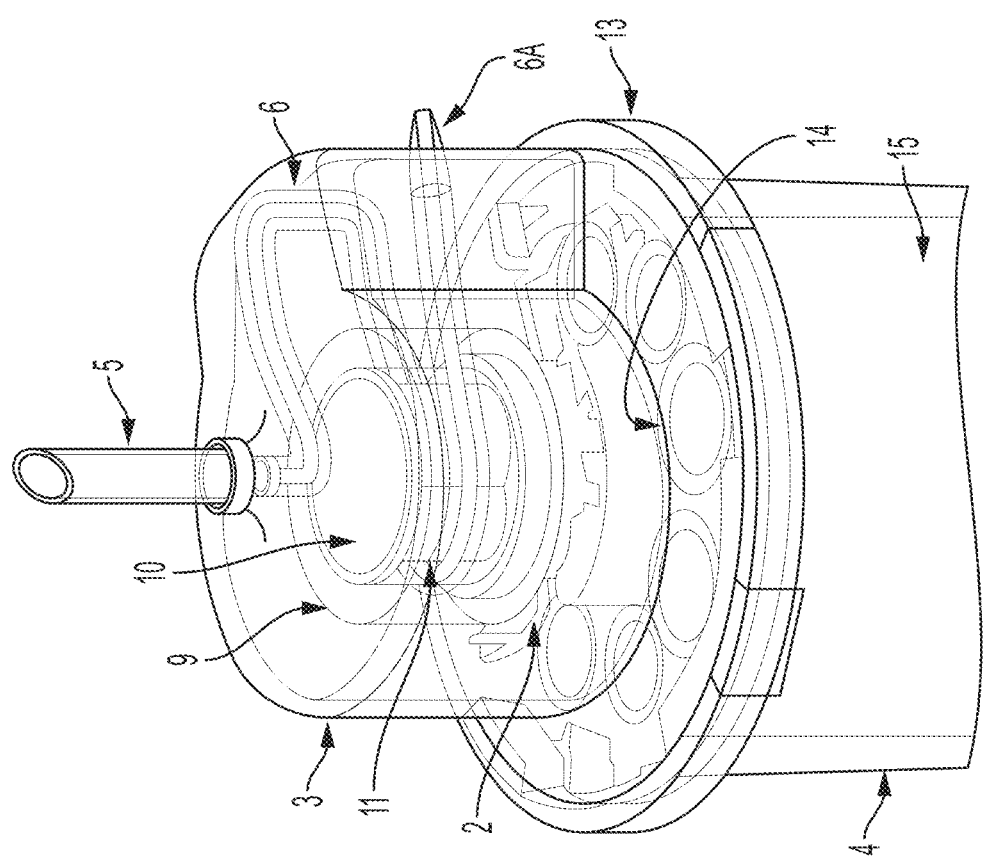
FIG. 3 illustrates an example of the top portion of the pump housing with transparent housing elements to view the internal components in accordance with some embodiments disclosed herein.
Figure 4A:
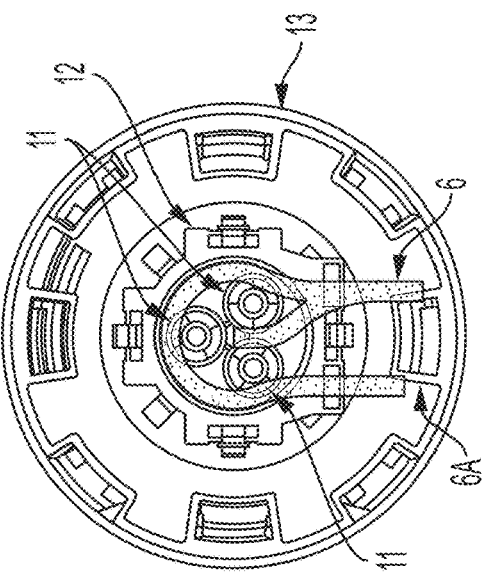
FIG. 4A illustrates a top view of the pump housing with the upper housing member removed in accordance with some embodiments disclosed herein.
Figure 4B:
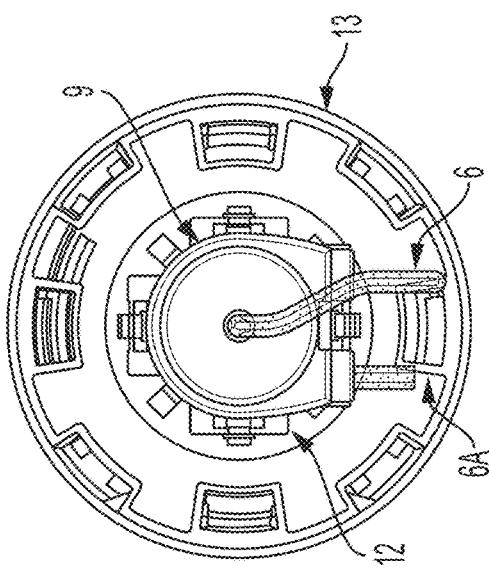
FIG. 4B illustrates a top view of the pump housing with the upper housing member, the peristaltic housing, and the roller holder removed in accordance with some embodiments disclosed herein.
Figure 4C:
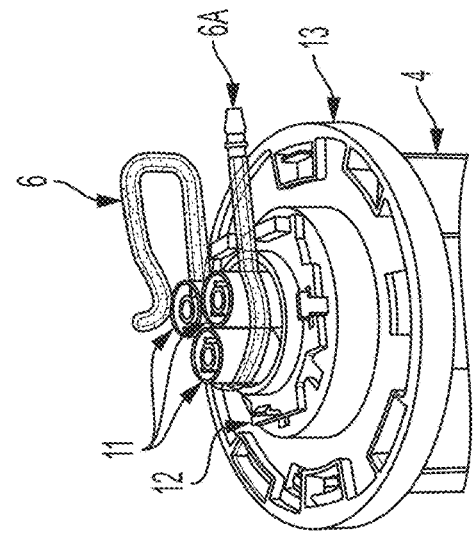
FIG. 4C illustrates a perspective view of the pump housing with the upper housing member removed in accordance with some embodiments disclosed herein.
Figure 4D:
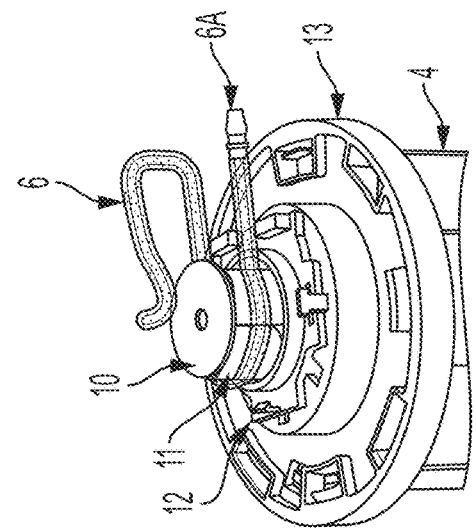
FIG. 4D illustrates a perspective view of the pump housing with the upper housing member and the peristaltic housing removed in accordance with some embodiments disclosed herein.
Figure 4E:
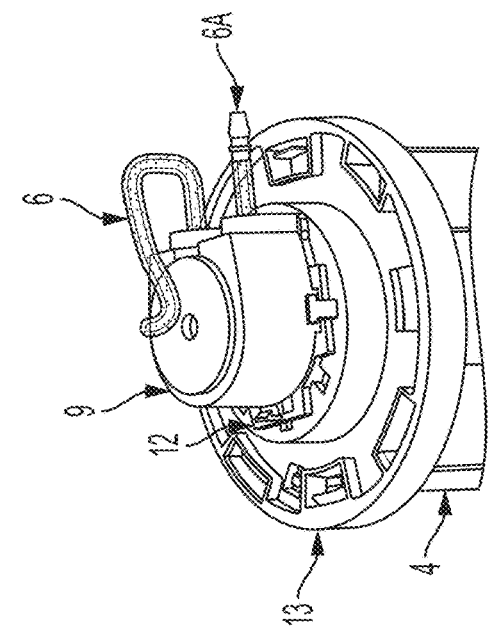
FIG. 4E illustrates a perspective view of the pump housing with the upper housing member, peristaltic housing, and the roller holder removed in accordance with some embodiments disclosed herein.
Figure 5A:
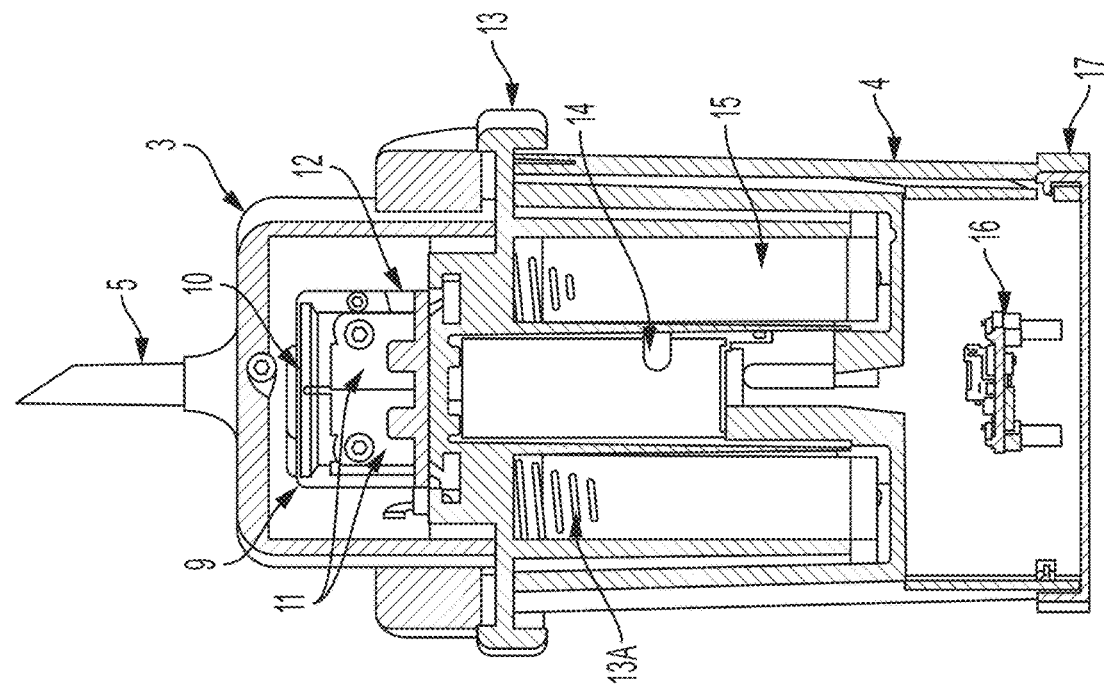
FIG. 5A illustrates a cross section of the pump housing in accordance with some embodiments disclosed herein.
Figure 5B:
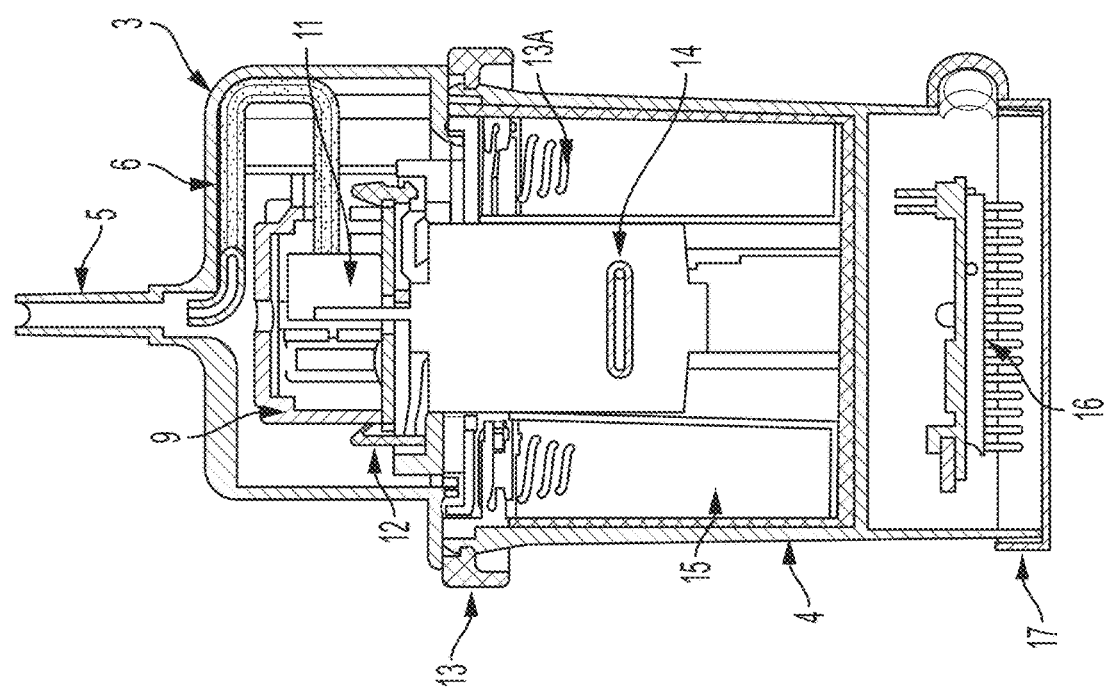
FIG. 5B illustrates a cross section of the pump housing in accordance with some embodiments disclosed herein.

The pump housing also contains a peristaltic pump. As shown in FIG. 2, the peristaltic pump can include a variety of components such as peristaltic housing 9, roller holder 10, rollers 11, peristaltic base 12, power source housing 13, motor 14, power source 15, and microcontroller 16. The roller holder can hold the rollers at a set distance from each other and from the center axis. The roller holder can prevent all but two degrees of freedom for the individual rollers. For example, the rollers can be freely able to individually rotate around their axis and translational movement in the Z direction is possible but is eventually controlled in the final assembly with the peristaltic base and peristaltic housing. The peristaltic base can have three main purposes: (1) It can lock with the peristaltic housing to prevent the Z-axis translational movement of the rollers; (2) It can connect to the middle motor/battery housing so that the full peristaltic assembly is locked in the correction orientation with the rest of the assembly; and (3) it can act as a guard to prevent the roller holder and rollers from slipping out of alignment.

In some embodiments, the motor can be a high RPM DC motor such as a DC 12V motor. The motor can include a motor shaft that drives the rollers. In some embodiments, the plurality of rollers can be cylindrical peristaltic rollers. In some embodiments, the plurality of rollers can include three rollers. The motor can drive the rollers and the power source can power/drive the motor. In some embodiments, the power source housing can be the middle housing member. In some embodiments, the power source can be a battery assembly. In some embodiments, the battery assembly can include AA batteries. In some embodiments, the power source housing can include conical battery connectors 13A for the battery assembly.

The peristaltic pump can also include flexible tubing 6. The peristaltic pump can function with the positive displacement of the fluid in the flexible tube through the use of the rollers. This can be made cost effective enough for a disposable system by utilizing a low cost, high RPM DC motor for the motor. Typical peristaltic pumps can directly rotate a plate that the rollers are mounted on which requires a high torque motor. However, by utilizing the rollers as planetary gears, the same functionality can be achieved with a high RPM, low torque motor.

For example, FIG. 7 illustrates a planetary motion diagram for the peristaltic pump used in the pump housing disclosed herein in accordance with some embodiments. FIG. 7 shows that the rollers can be squeezed against the motor shaft and the flexible tubing, thereby pinching off the flexible tubing. When the motor rotates, the rollers that are pressed against the motor shaft can rotate individually as well as in the opposite direction of the motor shaft. Due to the friction and forces pushing the rollers against the flexible tube and peristaltic housing that houses the rollers and flexible tubing, when the rollers individually rotate, it can cause their position to rotate around the axis of the motor. Due to the ratio of the sizes between the motor shaft, rollers, and the peristaltic housing, the rollers can move at a reduced speed from that of the motor, but the motor does not stall from this load. In some embodiments, the peristaltic pump can allow for bi-directional movement of fluid by controlling the motor direction. In addition, the peristaltic pump can have constant flow rates regardless of the pressure of the system.

The flexible tubing of the peristaltic pump can be fluidly connected to the fluid inlet of the upper housing member. The flexible tubing of the peristaltic pump can also be fluidly connected to a fluid outlet 6A. The fluid outlet can also be located on the upper housing member. In some embodiments, the fluid outlet is perpendicular to the fluid inlet as shown in FIG. 1. In some embodiments, the fluid outlet is on a side surface of the upper housing member. In some embodiments, the flexible tubing of the peristaltic pump can include a connector at the fluid outlet. The connector can be a tubing-to-tubing connector such that the flexible tubing of the peristaltic pump can be fluidly connected to tubing outside of the pump housing.

The upper housing member can cover or house the assembly of the peristaltic housing, roller holder, rollers, flexible tubing, and peristaltic base. The middle housing member/power source housing can be connected to the power source for the peristaltic pump. In addition, the bottom housing member can cover the power source, the motor, and the microcontroller.

The fluid outlet of the pump housing can be fluidly connected to tubing 6C as shown in FIG. 1. The inner diameter of the tubing external to the pump housing can be about 0.1-5 mm, about 0.2-4 mm, about 0.5-2 mm, about 0.75-2 mm, about 1-1.5 mm, or about 1.3 mm. The outer diameter of the tubing external to the pump housing can be about 0.5-10 mm, about 1-5 mm, about 2-4 mm, about 2.5-3.5 mm, or about 3 mm. The wall thickness of the tubing external to the pump housing can be about 0.1-2 mm, about 0.3-1.5 mm, about 0.5-1 mm, about 0.75-0.95 mm, or about 0.85 mm.

The rigidity of the tubing can prevent back pressure from building in the tubing. In some embodiments, the durometer of the PVC tubing used is 85 Shore A. A material with this durometer or higher can work if other dimensions are constant. A key challenge in the tubing is to prevent and/or substantially reduce the stretch of the tubing under the high internal pressure. The more the volume stretches, the more fluid can be released once the pump is turned off. This is not only a factor of the material properties, but also the wall thickness and diameter of the tubing (as well as the internal pressure). The combination of this material and the inner diameter and wall thickness can prevent and/or substantially reduce the volumetric stretch seen in other tubing for similar products.

The fluid outlet of the pump housing can also be fluidly connected to endoscope sheath 7. The endoscope sheath and the fluid outlet of the pump housing can be fluidly connected by tubing 6C. A distal end of the tubing can be fluidly connected to a proximal end of the endoscope sheath, whereas the proximal end of the tubing can be connected to the fluid outlet of the pump housing, as shown in FIG. 1. The endoscope sheath can be configured to receive an endoscope for use during an endoscopic procedure. In addition, the endoscope sheath can be configured to supply fluid to a distal end of an endoscope for cleaning the distal end of the endoscope. In some embodiments, the endoscope sheath is configured to dispense fluid on the distal tip of the endoscope. In some embodiments, the endoscope sheath can also be configured to remove fluid from the distal tip of the endoscope. In some embodiments, fluid can flow from the tubing connection of the sheath through the gap that is formed between the outer diameter of the scope and the inner diameter of the sheath. The distal end of the sheath can be designed to deflect the fluid onto the lens of the scope and also to aid in removing the fluid that remains on the lens of the scope after the cleaning cycle.

Figure 6:
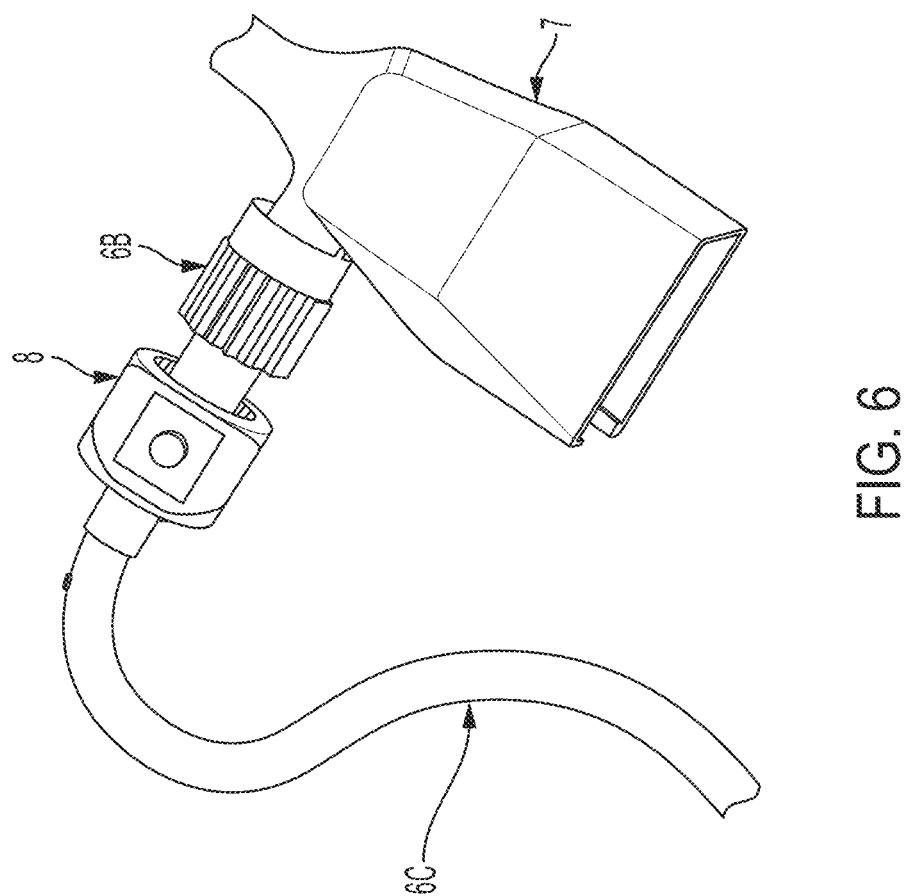
FIG. 6 illustrates a close up view of the pump control of the peristaltic endoscope cleaning system in accordance with some embodiments disclosed herein.
Figure 8B:
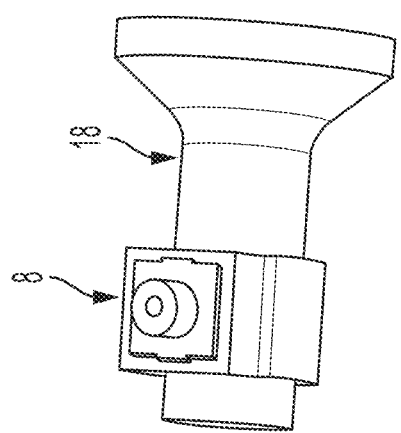
FIG. 8B illustrates a pump control attached to an eyepiece in accordance with some embodiments disclosed herein.
Figure 8A:
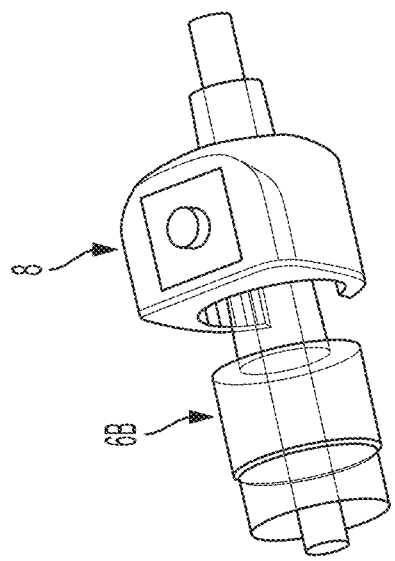
FIG. 8A illustrates a pump control attached to a luer connector in accordance with some embodiments disclosed herein.

In some embodiments, the pump control can be a foot-controlled switch. In some embodiments, the pump control can be a hand-controlled switch. As shown in FIGS. 8A and 8B, the pump control can be integrated into mechanical clips that are designed to be attached (e.g., snapped, screwed, hook-and-loop fastened, adhesively applied) onto specific areas on the device such as the shaft of the endoscope sheath or the tubing that connects the pump housing and the endoscope sheath. In some embodiments, the pump control is attached to a distal end of the tubing in close proximity to the proximal end of the endoscope sheath. As shown in FIG. 1 and FIG. 6, pump control 8 can be attached to tubing 6C. FIG. 8A illustrates pump control 8 connected to a luer connector 6B. The luer connector can fluidly connect tubing 6C and the endoscope sheath 7.

In some embodiments, the pump control can be attached to the endoscope sheath. For example, the pump control can be attached to the shaft of the endoscope sheath or the hub of the endoscope sheath. In some embodiments, the pump control can be attached to the proximal end of the endoscope sheath. In some embodiments, as shown in FIG. 8B, the pump control can be attached to the neck of the eyepiece 18 on the endoscope. The eyepiece can be the most proximal component of the endoscope. The neck of the eyepiece can be the thinner, cylindrical section of the eyepiece before it widens. In some embodiments, the eyepiece is what connects to the coupler on the camera. Putting a hand control at this location can be a possibility as surgeons tend to hold the device in a way that the switch would be easily accessible in this location. In some embodiments, the user can determine the location of the pump control in the peristaltic cleaning system.

The pump control can control the peristaltic pump. In some embodiments, the pump control can be configured to activate the peristaltic pump. In some embodiments, the pump control can be configured to control/regulate the direction of the peristaltic pump. In some embodiments, the pump control can be configured to control/regulate the speed of the peristaltic pump. As such, the pump control can be configured to control/regulate the speed and direction of the motor of the peristaltic pump, thereby controlling/regulating the speed and direction of the fluid through the peristaltic endoscope cleaning system.

The peristaltic pump can be communicatively coupled to pump control 8. As such, the microcontroller of the peristaltic pump can be communicatively coupled to pump control 8. The microcontroller can include a processor, memory, and input/output peripherals that can be used to control the peristaltic pump. In some embodiments, the peristaltic pump and the pump control are wirelessly communicatively coupled to each other. In some embodiments, the peristaltic pump and the pump control are communicatively coupled to each other by wire(s). When the peristaltic pump and the pump control are communicatively coupled to each other by wire(s), the wiring can be connected to tubing 6C such that the wiring runs the length of the tubing between the pump housing and the endoscope sheath. In some embodiments, the wiring and tubing can fork near the distal end of the tubing such that the tubing can connect to the endoscope sheath (e.g., tubing can connect to the luer connector that is connected to the endoscope sheath) and the wiring can connect to the pump control which can be attached to another nearby component such as the endoscope sheath itself. In some embodiments, the wiring and the tubing can be separate. For example, in the case when the pump control is a foot-controlled switch, the foot-controlled switch would not be near the tubing that connects the pump housing and the endoscope sheath.

In order for the endoscope to be clear of fluid, the fluid can be dispensed on the distal tip of the endoscope and then removed at the end of the cleaning cycle. This bi-directional movement of fluid is possible on a peristaltic pump capable of reversing the current through the motor to reverse the direction of the motor. In some embodiments, a cleaning cycle of the system and pump disclosed herein can have five phases. First, when the user activates the pump control (e.g., when the user activates the switch/button of the pump control), the microcontroller of the pump activates the motor to drive fluid to the distal end of the sheath which can be displaced onto the lens of an endoscope. In some embodiments, when the user activates the pump control, the peristaltic pump can be configured such that the motor can be driven at maximum speed temporarily in order for the fluid to reach the end of the tubing and sheath as quickly as possible.

Second, the peristaltic pump can be configured such that the motor continues to run in the forward direction, but at a reduced speed for optimized cleaning as long as the user is still activating the pump control (e.g., holding down the switch/button of the pump control). As such, the microcontroller of the peristaltic pump can be programmed to first run the motor briefly at a higher RPM to quickly drive fluid to the endoscope sheath and then reduce the RPM to provide a flow optimized for cleaning the endoscope while the pump control is still activated.

Third, when the user stops activation of the pump control (e.g., the user lets go of the switch/button of the pump control), the peristaltic pump can be configured such that the motor runs in the reverse direction at full speed to remove residual fluid from the endoscope as quickly as possible. As such, the microcontroller of the peristaltic pump can be programmed to reverse the current through the motor to run the pump in reverse when the activation of the pump control is released. When this occurs, the peristaltic rollers can spin in the opposite direction and withdraw fluid from the distal end of the endoscope sheath/endoscope. This serves to remove residual fluid form the distal end of the endoscope lens after cleaning.

Fourth, after this initial ramp reverse period, the peristaltic pump can be configured such that the motor has a secondary, temporary period where it runs in reverse at a lower speed (i.e., lower RPM) to reduce the amount of back pressure in the tubing. This can prevent fluid from dripping onto the lens when the peristaltic pump is not running. Lastly, the peristaltic pump can be configured to turn off after this second, temporary reverse period.

Figure 9:
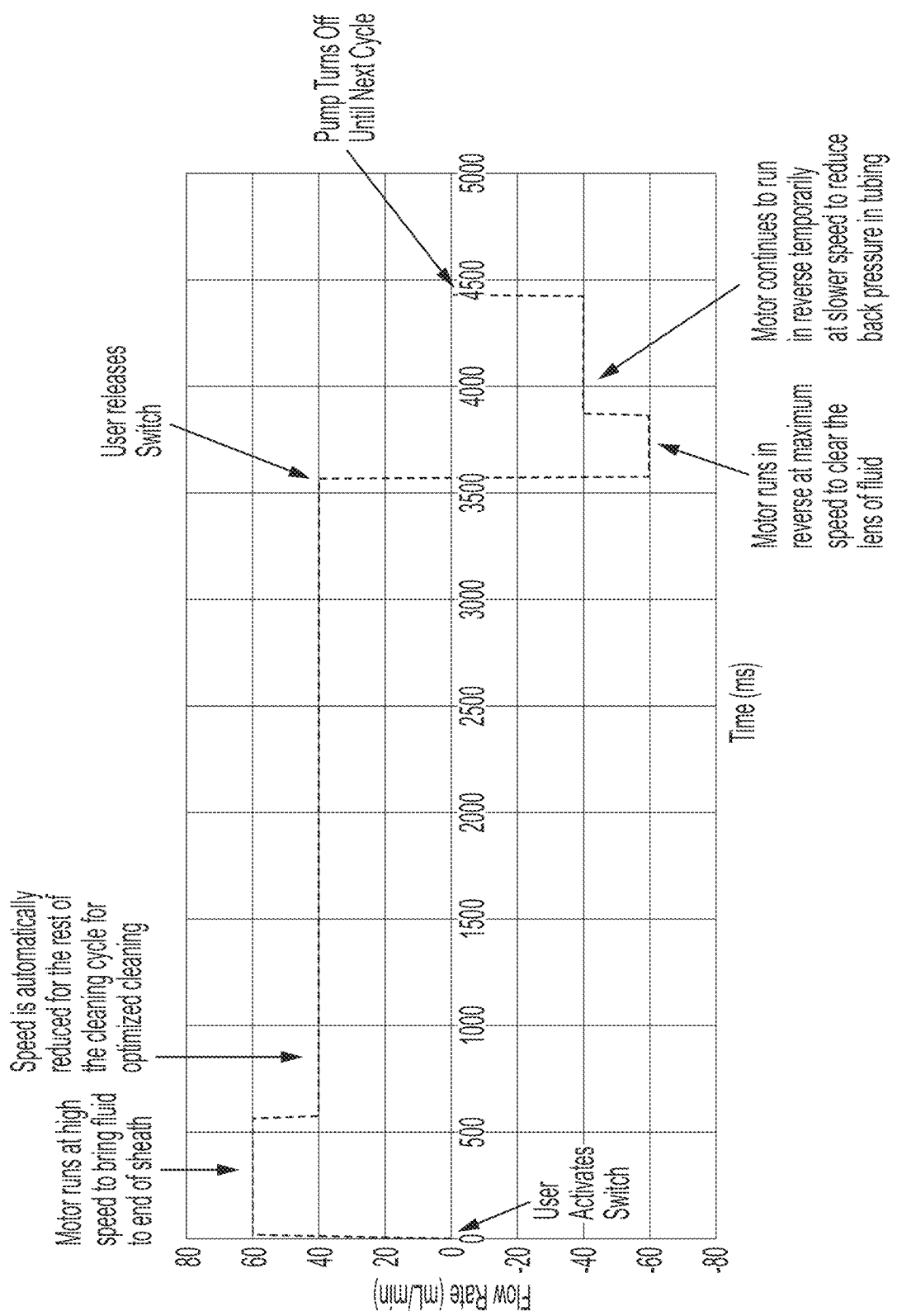
FIG. 9 illustrates an example of the five phase cleaning cycle for the peristaltic pump in accordance with some embodiments disclosed herein.

This five phase cycle described above can help reduce the amount of time for fluid to initially reach the endoscope lens while not compromising cleaning ability. In addition, it also can quickly remove fluid and help reduce back pressure in tubing. FIG. 9 illustrates the five phase cleaning cycle and peristaltic pump motor direction/speed described above. In some embodiments, the peristaltic pump can be configured to displace fluid from the inlet to the outlet of the pump housing at a first speed for a first period of time when the pump control is activated. In some embodiments, while the pump control is still activated, the peristaltic pump can be configured to displace fluid from the inlet to the outlet of the pump housing at a second speed that is less than the first speed when the first period of time is over. In some embodiments, the peristaltic pump can be configured to automatically displace fluid from the outlet to the inlet of the pump housing when the pump control is no longer activated.

In some embodiments, upon deactivation of the pump control, the peristaltic pump can be configured to displace fluid from the fluid outlet to the fluid inlet at a third speed for a second period of time. In some embodiments, while the pump control is still deactivated and when the second period of time is over, the peristaltic pump can be configured to displace fluid form the fluid outlet to the fluid inlet at a fourth speed that is less than the third speed. In some embodiments, the peristaltic pump can be configured to displace fluid from the fluid outlet to the fluid inlet at the fourth speed for a third period of time. When the third period of time is over, the peristaltic pump can be configured to turn off Accordingly, when a user activates the pump control (e.g., by pressing the switch/button on the pump control), the motor can be driven forward (fluid out of the system) at a relatively high speed to get the fluid to the end of the endoscope sheath, then the motor speed can be reduced for the cleaning cycle, and finally the motor can be driven backwards (fluid into the system) when the user deactivates the pump control (e.g., by releasing the switch/button on the pump control). Thus, the peristaltic pump can be configured to automate the forward and reverse direction of fluid upon user activation/deactivation of the pump control.

Accordingly, when the pump control is activated, the peristaltic pump can displace fluid from the fluid inlet to the fluid outlet of the pump housing (i.e., the pump can run in the forward direction). The fluid leaving the pump housing can travel through the tubing that connects the pump housing to the endoscope sheath. Once reaching the endoscope sheath, the fluid can travel towards the distal end of the endoscope sheath where it can be deposited on the endoscope (i.e., the endoscope lens) for cleaning. When the pump control is deactivated, the peristaltic pump can run in the reverse direction (i.e., the peristaltic pump can displace fluid from the fluid outlet to the fluid inlet). Thus, fluid that is located on the endoscope can be sucked back into the endoscope sheath where it will travel from the endoscope sheath towards the pump housing.

In some embodiments, the peristaltic pump can be connected to another device (e.g., a computer) separate from the peristaltic endoscope cleaning system. For example, the peristaltic pump can be communicatively coupled to another device, such as a camera control unit for the endoscope itself. This separate device can be configured to activate/deactivate the peristaltic pump rather than a pump control as previously discussed. In some embodiments, the peristaltic pump can be wirelessly communicatively coupled to this other device.

FIG. 10 illustrates a computer, in accordance with some embodiments. Computer 1000 can be a component of a device that can connect to the system for peristaltic endoscope cleaning as described herein. In some embodiments, computer 1000 may be configured to execute a method for controlling the peristaltic pump of the endoscope cleaning system, as described above.

Computer 1000 can be a host computer connected to a network. Computer 1000 can be a client computer or a server. As shown in FIG. 10, computer 300 can be any suitable type of microprocessor-based device, such as a personal computer; workstation; server; or handheld computer device, such as a phone or tablet. The computer can include, for example, one or more of processor 1010, input device 1020, output device 1030, storage 1040, and communication device 1060.

Input device 1020 can be any suitable device that provides input, such as a touch screen or monitor, keyboard, mouse, or voice-recognition device. Output device 1030 can be any suitable device that provides output, such as a touch screen, monitor, printer, disk drive, or speaker.

Storage 1040 can be any suitable device that provides storage, such as an electrical, magnetic, or optical memory, including a RAM, cache, hard drive, CD-ROM drive, tape drive, or removable storage disk. Communication device 1060 can include any suitable device capable of transmitting and receiving signals over a network, such as a network interface chip or card. The components of the computer can be connected in any suitable manner, such as via a physical bus or wirelessly. Storage 1040 can be a non-transitory computer-readable storage medium comprising one or more programs, which, when executed by one or more processors, such as processor 1010, cause the one or more processors to execute methods described herein, such as all or part of the methods described above with respect to controlling the peristaltic pump.

Software 1050, which can be stored in storage 1040 and executed by processor 1010, can include, for example, the programming that embodies the functionality of the present disclosure (e.g., as embodied in the systems, computers, servers, and/or devices as described above). In some embodiments, software 1050 can be implemented and executed on a combination of servers such as application servers and database servers.

Software 1050 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 1040, that can contain or store programming for us by or in connection with an instruction execution system, apparatus, or device.

Software 1050 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 1000 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 1000 can implement any operating system suitable for operating on the network. Software 1050 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example. The above explanation of computer 1000 can also apply to the microcontroller of the peristaltic pump.

For the purpose of clarity and a concise description, features are described herein as part of the same or separate embodiments; however, it will be appreciated that the scope of the disclosure includes embodiments having combinations of all or some of the features described.

DEFINITIONS

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Reference to "about" a value or parameter herein includes (and describes) variations that are directed to that value or parameter per se. For example, description referring to "about X" includes description of "X". In addition, reference to phrases "less than", "greater than", "at most", "at least", "less than or equal to", "greater than or equal to", or other similar phrases followed by a string of values or parameters is meant to apply the phrase to each value or parameter in the string of values or parameters.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may specially constructed for the required purposes, or it may comprise a general purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMS, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each connected to a computer system bus. Furthermore, the computing systems referred to in the specification may include a single processor may be architectures employing multiple processor designs, such as for performing different functions or for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The structure for a variety of these systems can appear from the description above. In addition, the present disclosure is not described with reference to any particular programming language. It will be appreciated that a variety of programming languages may be used to implement the teachings of the present invention as described herein.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

The above description is presented to enable a person skilled in the art to make and use the disclosure, and is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein.

The invention claimed is:

1. An endoscope cleaning system comprising:
a pump housing comprising a fluid inlet, a fluid outlet, and a peristaltic pump configured to displace fluid from the fluid inlet to the fluid outlet;
an endoscope sheath fluidly connected to the fluid outlet of the pump housing, wherein the endoscope sheath is configured to receive an endoscope; and
a microcontroller configured to execute:
upon activation of the peristaltic pump, the peristaltic pump displaces fluid from the fluid inlet to the fluid outlet at a first speed for a first period of time;
while the peristaltic pump is still activated and upon termination of the first period of time, the peristaltic pump displaces fluid from the fluid inlet to the fluid outlet at a second speed, wherein the second speed is less than the first speed;
upon deactivation of the peristaltic pump, the peristaltic pump displaces fluid from the fluid outlet to the fluid inlet at a third speed for a second period of time; and
while the peristaltic pump is deactivated and upon termination of the second period of time, the peristaltic pump displaces fluid from the fluid outlet to the fluid inlet at a fourth speed for a third period of time, wherein the fourth speed is less than the third speed.

2. The cleaning system of claim 1, wherein the peristaltic pump comprises a plurality of peristaltic rollers and a motor to drive the peristaltic rollers.

3. The cleaning system of claim 2, wherein the peristaltic pump comprises a battery assembly to power the motor.

4. The cleaning system of claim 1, wherein the endoscope sheath and the fluid outlet of the pump housing are fluidly connected by tubing.

5. The cleaning system of claim 4, wherein the tubing is fluidly connected to a proximal end of the endoscope sheath.

6. The cleaning system of claim 1, wherein the endoscope sheath is configured to supply fluid to a distal end of an endoscope.

7. The cleaning system of claim 1, wherein the fluid inlet comprises a spike on a top surface of the pump housing.

8. The cleaning system of claim 7, wherein the spike is a hollow, tapered spike.

9. The cleaning system of claim 8, wherein the hollow, tapered spike is configured to be inserted into a fluid source.

10. The cleaning system of claim 9, wherein the fluid source is a sterile irrigation bag.

11. The cleaning system of claim 1, wherein the fluid outlet is perpendicular to the fluid inlet.

12. The cleaning system of claim 1, wherein the microcontroller is configured to execute: while the peristaltic pump is deactivated and upon termination of the third period of time, the peristaltic pump shuts off.

13. A method of cleaning an endoscope, comprising:
providing the endoscope cleaning system of claim 1;
activating a pump control;
upon activation of the pump control, displacing, via the peristaltic pump, fluid from the fluid inlet to the fluid outlet of the pump housing;
deactivating the pump control; and
upon deactivation of the pump control, displacing, via the peristaltic pump, fluid from the fluid outlet to the fluid inlet of the pump housing.

14. The method of claim 13, wherein upon activation of the pump control, the peristaltic pump displaces fluid from the fluid inlet to the fluid outlet at the first speed for the first period of time.

15. The method of claim 14, wherein while the pump control is activated and upon termination of the first period of time, the peristaltic pump displaces fluid from the fluid inlet to the fluid outlet at the second speed, wherein the second speed is less than the first speed.

16. The method of claim 13, wherein upon deactivation of the pump control, the peristaltic pump displaces fluid from the fluid outlet to the fluid inlet at the third speed for the second period of time.

17. The method of claim 16, wherein while the pump control is deactivated and upon termination of the second period of time, the peristaltic pump displaces fluid from the fluid outlet to the fluid inlet at the fourth speed, wherein the fourth speed is less than the third speed.

18. The method of claim 17, wherein the peristaltic pump displaces fluid from the fluid outlet to the fluid inlet at the fourth speed for the third period of time.

19. The method of claim 18, wherein upon termination of the third period of time, the peristaltic pump shuts off.

20. The method of claim 13, further comprising inserting an endoscope into the endoscope sheath.

21. The method of claim 13, further comprising inserting the fluid inlet of the pump housing into a fluid source.

22. The method of claim 21, wherein the fluid inlet is a hollow, tapered spike.

23. The method of claim 22, wherein the fluid source is a sterile irrigation bag.

24. The method of claim 13, wherein the pump control is communicatively coupled to the peristaltic pump.

25. The method of claim 24, wherein the pump control is wirelessly communicatively coupled to the peristaltic pump.

26. The method of claim 13, wherein while the pump control is activated, fluid is supplied from the endoscope sheath to a distal end of an endoscope.

27. The method of claim 13, wherein while the pump control is deactivated, fluid is removed from the distal end of the endoscope to the endoscope sheath.

* * * * *